United States Patent [19]

Trépo

[11] 4,087,519

[45] May 2, 1978

[54] MEDICAMENT FOR THE TREATMENT OF HEPATITIS AND/OR ACUTE OR CHRONIC INFECTIONS DUE TO THE VIRUS OF HEPATITIS B

[75] Inventor: Christian G. Trépo, Bron, France

[73] Assignee: Institut Merieux, Lyon, France

[21] Appl. No.: 752,790

[22] Filed: Dec. 20, 1976

[30] Foreign Application Priority Data

Dec. 23, 1975 France .................................. 75 39493

[51] Int. Cl.² ...................... A61K 39/42; A61K 39/12; C07G 7/00

[52] U.S. Cl. .................................. 424/86; 260/112 B; 424/89

[58] Field of Search ....................... 424/86; 260/112 B

[56] References Cited

U.S. PATENT DOCUMENTS 3,830,909  8/1974  Hayakawa ......................... 260/112 B

*Primary Examiner*—Sam Rosen

*Attorney, Agent, or Firm*—Cushman, Darby & Cushman

[57] ABSTRACT

This invention relates to a medicament which contains a gamma-globulin preparation containing anti-e antibodies. This medicament can be used for eliminating or reducing the infectiousness of biological liquids containing antigen-e or the virus of hepatitis B and can also be administered intramuscularly or intravenously to treat hepatitis and/or acute or chronic infections caused by the virus of hepatitis B in humans and animals.

9 Claims, No Drawings

MEDICAMENT FOR THE TREATMENT OF HEPATITIS AND/OR ACUTE OR CHRONIC INFECTIONS DUE TO THE VIRUS OF HEPATITIS B

The present invention relates to a medicament which makes it possible to treat acute or chronic infections due to the virus of hepatitis B (also called virus HB or virus B).

Following the identification, in the serum of the majority of the subjects suffering from viral hepatitis B, of an apparently specific antigen of virus B, called antigen Australia, it has been proposed to use this antigen, in a purified and, if appropriate, attenuated form, for the preparation of a vaccine against hepatitis caused by virus B (see French Patent Specification No. 70/34,574).

Antigen Australia is not itself the virus of hepatitis B. In fact, it has been found that the majority of blood donors who are asymptomatic carriers of antigen Australia have only little or no virus circulating in their serum.

It is known that the serum of numerous subjects, who are carriers of antigen Australia, contains another antigen which has been called antigen-e, abbreviated to Ag-e, [see L. O. Magnius and Ake Espmark, Acta. path. microbiol. scand., Section B, 80 335-337 (1972) which is incorporated herein by reference.]

Specimens of antigen-e are to be found at the Department of Virology, Statens Bakteriologeska Laboratorium, Stockholm and at the Liver Study Unit of Yale University, U.S.A.

The term antigen-e is applied to an antigen complex which represents a group of soluble proteins (called $e_1$, $e_2$ and so on) which are normally absent from human serum but are found in the serum of certain carriers of antigen Australia, in particular those who suffer from chronic hepatitis. Antigen-e is also found in haemodialysed or immunodepressed subjects or subjects suffering from mongolism. These various antigen determinants are immunologically distinct from antigen Australia.

In the present application, the term antibody anti-e is applied to antibodies which react with the proteins which constitute antigen-e. These antibodies can be found in the serum of subjects who have been contaminated with virus B, in particular in the serum of chronic carriers of antigen Australia who do not suffer from liver diseases or who are convalescing recovering from acute hepatitis.

It has been found that the administration of antigen-e is capable of bringing about an immunological response, with formation of antibody anti-e.

It has now been found according to this invention that the administration of the anti-e antibodies to subjects suffering from acute and chronic infections, due to virus B in particular, makes it possible to cause the symptoms and histological lesions of hepatitis to disappear.

It has also been discovered that the addition of anti-e antibodies to biological liquids containing antigen-e and/or virus B makes it possible to cause the infectiousness of these liquids to disappear, or to reduce it very considerably.

Currently, no active treatment of acute hepatitis exists. Neither does a therapy exist which is capable in particular of preventing the sudden fatal aggravation of such hepatitis or their chronic development towards cirrhosis.

The same is true in the case of chronic infections due to latent or non-latent HB virus (chronic hepatitis, nodal periarteritis and glomerulonephritis caused by virus HB).

When used in this second group of diseases, the antiinflammatorymedicaments (corticosteroids) and immunosupressants only exert a beneficial action in respect of reducing the inflammatory reaction, but they have no effect whatsoever on the viral infection responsible for the disease, and on the contrary they favor the persistence of this infection.

The discovery of the efficiency of the anti-e antibodies in the treatment of hepatitis caused by virus B is surprising because hitherto attempts to inject, into man or chimpanzees, plasma containing anti-HBs antibodies directed against a surface antigen of the virus of hepatitis B (an antigen called Ag HBs) in the hope of ameliorating hepatitis or chronic viraemia have always failed. The transfusion of plasmas selected for their high content of anti-HBs antibodies thus appears not to have a therapeutic action under the conditions where it has been possible to use them; see, for example, Reed et al., Lancet, 2, 1347 (1973), C. G. Trepo, The American Journal of the Medical Sciences, 270, 248 (1975) and "Treatment of Fulminant hepatitis with hepatitis B immune globulin: a cooperative study", Gastroenterology, 66, A 98-752 (1974).

The present invention provides a medicament, which contains, in a physiologically acceptable medium, a gamma-globulin preparation containing anti-e antibodies, the said preparation being obtained from serum or from blood plasma or from placentary extracts.

It is known that the antibodies formed by an organism in response to the administration of an antigen constitute a family of proteins which have numerous characteristics in common and which are called gamma-globulins.

The gamma-globulin preparations containing anti-e antibodies can be obtained in accordance with conventional processes for the preparation of gamma-globulins from serum, from plasma, or from placentary extracts in which the presence of anti-e antibodies has been detected beforehand. These conventional processes are in particular those described by H. J. Cohn et al., J.A.C.S., 68, 459 (1946); J. L. Oncley et al., J.A.C.S., 71, 541 (1949); H. L. Taylor et al., J.A.C.S., 78, 1356 (1956); J. Horhjsi and R. Smetana, Acta Medica Scandinavia, Vol. CLV, 65 (1956); and P. Kistler and Hs. Nitschmann, Vox Sang., 7, 414 (1962). The anti-e antibodies can be found either in subjects who have spontaneously developed these antibodies or in volunteer subjects who have been immunized with a purified antigen-e preparation devoid of any risk of infection, and who have formed anti-e antibodies by immunological response. The presence of the anti-e antibodies can be detected in particular with the aid of a reagent containing antigen-e, using the immunodiffusion or electroimmunodiffusion technique or any other conventional serological technique, for example radioimmunological determination.

In order to bring about the formation of anti-e antibodies by immunological response, or in order to detect the presence of the said antibodies, it is advantageous to have available partially or completely purified preparations of antigen-e which can be obtained, for example, by affinity chromatography on an immuno-adsorbent consisting of a support of porous material of which the surface is lined with a covering of anti-e antibody particles bonded to the support by means of a coupling agent.

The support may consist, for example, of Sepharose, and the coupling agent may be, for example, a cyanogen halide. It is possible to use, in particular, a support of Sepharose 4 B, the coupling agent being preferably cyanogen bromide.

Of course, it is possible to use other porous supports already known to be usuable in immuno-adsorption processes, with coupling agents which are also known, and which may be, for example, bifunctional derivatives such as dialdehydes.

The purified fractions containing the antigen-e can also be obtained by a process comprising at least one of the following stages, if appropriate, in combination with the immuno-adsorption stage:
a stage of filtration over a gel;
a stage of ultrafiltration using a membrane having a pore size such that it retains molecules having a molecular weight greater than 30,000; and
a preparative zonal ultra-centrifugation stage carried out, for example, in a sucrose gradient.

It is particularly possible to use a process in which a column containing Sepharose, coupled to the anti-e antibody, is equilibrated with a borate buffer at pH 8.4. A solution containing the antigen-e in the same buffer is added to the column, the solution is left in contact for sufficient time to favour maximum adsorption, and the antigen-e is then eluted with a phosphate buffer of pH about 10.8 – 10.9.

Thereafter, the fractions containing the antigen-e are collected, the presence of the antigen-e proteins being determined, for example, by measuring the optical density at 280 nm.

The purified fractions of antigen-e are then suitably brought to a physiological pH by adding hydrochloric acid, after which these fractions are concentrated, if desired, by ultrafiltration, and the presence of Ag-e is confirmed by immunodiffusion.

As indicated above, the fraction containing antigen-e can also be prepared by zonal ulta-centrifugation in a sucrose gradient. To do this, the serum or the defibrinated starting plasma is suitably concentrated 2-fold to 10-fold, preferably 5-fold, for example by precipitating the proteins by means of polyethylene glycol and redissolving them in a buffered aqueous solution. The solution thus obtained is deposited on the surface of tubes containing a linear sucrose gradient of 10 to 27% and is subjected to preparative zonal centrifugation at 19,000 – 22,000 revolutions per minute at between 4° and 8° C for 18 to 25 hours. Thereafter, fractions are collected, starting from the bottom of the tube, and the fractions containing the antigen-e are combined. This ultracentrifugation can be repeated to give a greater purification and can be completed by filtrations over a gel. Thereafter, the combined Ag-e fractions can be dialysed against a phosphate buffer. Thereafter, if desired, the material can be concentrated by ultrafiltration using a filter equipped with a membrane of which the pore size is such that it retains the products of molecular weight greater than 30,000.

The solution obtained can be administered to humans, subcutaneously or intramuscularly, after having been subjected, by way of precaution, to a treatment intended to remove a possibly infectious residue by the conventional processes of heating, or of treatment with formaldehyde, or of irradiation with ultraviolet rays or any other irradiation. A physiologically acceptable antigen-e fraction is thus obtained.

In order to provoke an antibody response in the volunteers, the physiologically acceptable fraction of antigen-e can be administered either by itself or in combination with an adjuvant such as aluminum hydroxide, aluminum phosphate or any other natural or synthetic adjuvant.

The starting product for the preparation of the purified fraction containing the antigen-e is a solution originating either from serum or from defibrinated plasma and giving a precipitation reaction with the anti-e antibody. The detection and isolation of the anti-e antibody are in this case carried out as indicated below.

The antigen-e, detected by Magnius and Espmark, loc. cit., is present transiently in the blood of patients suffering from acute hepatitis B and persistently in the blood of numerous haemodialysed subjects or subjects suffering from chronic hepatitis B, and to a varying degree in other asymptomatic carriers of Ag-Australia, in particular in certain ethnic groups or in certain geographic regions, for example, Asia.

In order to prepare a purified fraction of antigen-e, the serum or the plasma of these donors, if appropriate taken by plasmapheresis, may thus be used.

It will be recalled that the presence of antigen-e can be detected by immunodiffusion, as described by Magnius and Espmark in the article cited above, or by counterelectrophoresis.

In order to detect the presence of antigen-e, it is also possible to prepare a reagent containing anti-e antibodies by administering a purified antigen-e preparation, such as that described above, in combination with complete Freund adjuvant or any other adjuvant, to an animal, at least one administration, and preferably several, being carried out, after which administration by injection is repeated about every month, for example for three months. Each time, the purified antigen-e/Freund adjuvant combination is administered. The formation of anti-e antibodies in the animal is thus brought about.

The blood of the animal is then drained, partially or completely, and the serum is collected. A check is made to ensure that this serum does not contain normal human anti-protein antibodies.

In immunodiffusion, the reagent consisting of the serum obtained will give a precipitation line with a serum of human origin if the latter contains antigen-e.

If the human serum tested gives a precipitation line with this reagent, the subject is infected and is probably suffering from persistent hepatitis.

The repeated detection, by this method, of the presence of antigen-e during the acute phase of a hepatitis, and above all the persistence of the antigen-e, suggests an increased risk of development into chronic hepatitis.

It is in this way possible to detect the contagious infected subjects and furthermore detect, at an early stage and by a simple method, the risks of development into chronic hepatitis.

The anti-e antibody intended to demonstrate the presence of antigen-e can originate either from a human being or from an animal. For the purification of antigen-e intended for the preparation of vaccine for man, it is preferred to use a support coupled to an anti-e antibody of human origin.

The detection of the anti-e antibody is carried out as indicated by Magnius and Espmark, loc. cit., or by any other serological method.

The anti-e antibody can be obtained, for example, by zonal centrifugation of a serum in which the presence of this antibody has been detected beforehand, or, preferably, in accordance with the conventional method for the preparation of the gamma-globulins; see the references mentioned above. It is possible to use known techniques of fractionation using ethanol, ammonium sulphate and/or Rivanol. For example, the antibody can be precipitated by adding a solution of ammonium sulphate which is 40% saturated, redissolving the precipitate and subjecting the latter to a dialysis to remove the ammonium sulphate.

By way of a non-limiting illustration of these known methods, an Example of fractionation using ethanol is given later.

The medicament of this invention preferably contains a purified preparation of anti-e antibody, the said preparation having been freed from substantially all normal blood protein constituents other than gamma-globulins and from substantially all infectious contaminants.

However, the medicament according to the invention can also consist of whole plasma or whole serum, in which the presence of this antibody has been detected.

The gamma-globulins containing the anti-e antibodies which can be used as active ingredients in the medicament of the invention can also have undergone conventional transformations which allow the gamma-globulins to be administered intravenously. It is known that these treatments consist of eliminating or reducing the anti-complementary power of the gamma-globulins, this anti-complementary power being due to the presence of aggregates which can fix the complement, as does the antigen-antibody complex. Various processes which make it possible to obtain gamma-globulins which are intravenously injectable are known. These processes consist, for example, of subjecting the gamma-globulin either to an incubation or to an enzymatic digestion with pepsin, papaine or plasmin.

The medicament according to the invention can in particular be administered in the course of acute hepatitis or acute virus B infections in order to hasten their cure and to prevent any risk of a chronic development.

The medicament may be injected intramuscularly or intravenously.

The treatment with the anti-e gamma-globulins can be used by itself or in association with various anti-allergic, anti-inflammatory or other medications. One or more successive injections may be given, depending upon the biological and serological results.

The medicament of the invention can also be administered in the course of the various types of hepatitis and of any chronic virus B infections. These illnesses are diagnosed by the usual clinical, biological, histological and serological methods, in particular by the detection of the Ag-HBs.

These conditions may furthermore be characterised serologically by the absence of a satisfactory anti-e antibody response and even, in most cases, by a persistence of the Ag-e.

Chronic active hepatitis represent the most serious form of these conditions and they can be treated by anti-e antibodies.

The administration of anti-e antibody will necessarily be more prolonged in these forms of chronic illnesses.

Intravenous administration will at times be necessary and plasma containing anti-e antibodies can be used in place of gamma-globulins suitable for intravenous administration. Where a large amount of antigen-e is circulating, it is possible first to eliminate this circulating antigen-e by a prior exsanguino-transfusion, or a continuous plasmapheresis during which the plasma containing the Ag-e is replaced by iso-group plasma devoid of Ag-e and of antigen Australia, or the Ag-e is retained on a suitable filter, for example a porous support coupled to anti-e antibodies.

At the end of the operation, a fraction of the plasma of the patient may be replaced by plasma rich in anti-e antibodies or any other human protein, for example, albumin or other protein solution containing anti-e gamma-globulins treated for intravenous administration. The administration of anti-allergic and anti-inflammatory medications such as corticosteroids and antihistamines will avoid any troublesome reaction during this operation; this can be repeated in case of failure and above all can be completed by a further treatment with anti-e gamma-globulins.

This therapy can be coupled with auxiliary treatments of all kinds, such as chemotherapy or immunotherapy.

Whether the treatment of chronic hepatitis by anti-e antibodies should be an intravenous or intramuscular treatment, with or without exsanguinotranfusion, by itself or coupled with other treatments, may be decided on the basis of the result of a complete clinical and immunobiological assessment of the patient.

The presence of the virus HB and its fragments and associated antigens (Ag-Australia, Ag-HBC and Ag-e) in the serum and in the liver of the patient may be established by serological examinations and by studies of hepatic biopsies by immunofluorescence or under an electron microscope.

The study of the humoral and cellular immune responses directed against these three antigens can be assessed by serological titration of the antibodies and by tests on delayed hypersensitivity towards these same antigens, for example, inhibition of the migration of the leucocytes and possibly an intradermo-reaction with the three purified noninfectious antigens, namely Australia, HBC and e.

The results of all these tests as well as of those which explore the state of the overall immune responses of the patient will serve to decide the type of treatment to be employed, the posology being decided in accordance with the usual methods of determination of the posology for treatments with gamma-globulins.

At suitable doses, the anti-e gamma-globulins can be used as a preventive treatment of spontaneous, post-transfusion or other infections with virus HB, by being injected into the exposed subjects or added to the blood or its constituents before or after a possible fractionation to make the material suitable for injection in man, in order to neutralize the HB virus.

As has been indicated above, the antigen-e is in reality an antigen complex representing a group of proteins. Two of these proteins have been designated Ag-$e_1$ and Ag-$e_2$ by Alan Williams and Georges Le Bouvier, International Symposium on sub-types of antigen HBs, held at the National Blood Transfusion Centre in Paris, 14–18 April 1975, minuted in Bibliotheca Hematologica, 42, 65–70 (1976), which is incorporated herein by reference.

Others exist, and can, for example, be designated $e_3$ and so on. It has been found that the respective proportions of the various antigens-e vary with the carriers of antigen-e. Equally, the relative proportions of the various antibodies anti-$e_1$, anti-$e_2$ and so on can vary. By immunizing subjects with a preparation of Ag-e rich in one of the constituents of the antigen complex or by selecting plasmas of subjects, who are already carriers of anti-e antibodies, rich in one of the corresponding antibodies, it is possible to obtain gamma-globulin preparations containing predominantly one of these antibodies.

Preferred gamma-globulin preparations are those, for example, containing predominantly anti-$e_1$ or anti-$e_2$ antibody.

Another application of the gamma-globulin fractions containing anti-e antibodies is the elimination of infectious complete HB viruses and of antigens-e from any biological liquids which contain or may contain these, by agglutination and/or neutralization effected by contacting these with anti-e antibodies, for example by adding the anti-e antibodies to the said liquids. For example, the gamma-globulin preparation containing anti-e antibodies can be added to bottles of blood or plasma or any other biological liquid which is to be used for emergency perfusion and of which the harmlessness, that is to say, in the present case, the absence of virus HB, cannot be verified because there is not enough time. It is also possible to pass the said biological liquids over an immuno-adsorbent of which the surface is coated with anti-e antibody particles. To do this, it is possible, for example, to carry out an affinity chromatography analogous to that mentioned above in connection with obtaining partially or completely purified preparations of antigen-e, that is to say chromatography on a porous support coupled to anti-e antibodies. The regeneration of the support by elution of the adsorbed antigen furthermore makes it possible to obtain Ag-e preparations of which the usefulness has been referred to above.

In this case, the medicament of the invention consists of the blood, the plasma or any other biological liquid to be perfused, to which has been added the gamma-globulin preparation containing anti-e antibodies, or which has been passed over an immuno-adsorbent lined with anti-e antibody particles.

Of course, the gamma-globulin preparations added to the biological liquids have will have been subjected to a treatment which allows them to be administered intravenously.

The invention also relates to a process for the treatment of hepatitis and/or acute or chronic infections caused by virus hepatitis B, in which a medicament such as defined above is administered intramuscularly or intravenously to an infected human or animal.

The Examples which follow serve to illustrate the invention.

EXAMPLE 1:

Purification of the antigen-e by zonal ultracentrifugation

The plasma of subjects who are carriers of antigen-e is selected as described above, for example by an immunodiffusion identity reaction, preferably to antigen-e.

Calcium chloride is added to the plasma and the latter is left to stand for 24 hours in order to remove the fibrin. Polyethylene glycol of molecular weight between 6,000 and 7,500 (CARBOWAX 6,000) is added up to a 13% final conentration (weight/volume) in an 0.02% strength disodium phosphate buffer at pH 7.

After 24 hours at $+4°$ C, the precipitate is separated from the supernatant liquor by careful decantation. The greater part of the polyethylene glycol is then removed by adjusting the pH of the precipitate to 5 in an 0.25 M sodium acetate buffer. The precipitate is separated off, after 24 hours at $+4°$ C, by centrifuging at 4,000 revolutions per minute. The supernatant liquor, which contains the Ag-e, is introduced into a Sephadex G200 column and the fractions are collected.

The fractions which are found positive for Ag-e by immunodiffusion and/or electroimmunodiffusion are combined and concentrated by ultrafiltration on an Amicon apparatus equipped with a filter for molecular weight 30,000.

The solution concentrated in this way is deposited on the surface of three tubes containing a linear sucrose gradient of 10 to 30% (weight/weight) in a phosphate buffer of pH 7.4 and is subjected to preparative zonal centrifugation at 20,000 revolutions per minute at 4° C for 18 hours. Fractions of 3 ml are collected from the bottom of the tube. The fractions which are positive for antigen-e (for example, by the immunodiffusion test) are combined. The centrifugation can be repeated analogously on these fractions which are positive for Ag-e, in order to increase the degree of purification. Thereafter, a dialysis is carried out against a phosphate buffer of pH 7.4 for 24 hours, after which the material is concentrated by ultrafiltration with a filter equipped with a membrane of which the pore size is such that it retains the molecules of molecular weight greater than 30,000.

The solution of antigen-e obtained can be used to cause the formation of anti-e antibody after having been subjected, by way of precaution, to an attenuation by the action of heat, formaldehyde, beta-propiolactone or ultraviolet radiation, measured and combined so as to eliminate any possible residual infectiousness without destroying the antigenicity.

EXAMPLE 2:

Purification of antigen-e by affinity chromatography (a) Preparation of a Sepharose/anti-e immunoadsorbent The gamma-globulin fraction of a serum giving a positive anti-e test is prepared by precipitation with ammonium sulphate at pH 7, at 40% saturation.

The precipitate is redissolved. in 0.1 M NaHCO$_3$ buffer and is dialysed against an 0.5 M NaCl/0.1 M NaHCO$_3$ solution.

The anti-e gamma-globulins are coupled to Sepharose 4 B activated with cyanogen bromide (PHARMACIA-FINE UPSALA, Sweden) in accordance with the process described by Cuatrecas and Afinsen in ANN. REV. BIOCHEM. 40, 259 (1971).

7 g of Sepharose 4 B activated with CNBr are allowed to swell and are washed on a glass filter with 0.001 M HCl for 30 minutes. Immediately after washing, the gel is mixed with 200 mg of anti-e gamma-globulins in bicarbonate solution and the mixture is stirred for 2 hours at ambient temperature.

The gel is then washed with 600 ml of the 0.1 M NaHCO$_3$ solution containing 0.5 M NaCl and is treated with 50 ml of a 1 M ethanolamine solution at pH 8 for 2 hours at 25° C. The Sepharose coupled in this way is then washed alternately with a 1 M NaCl/0.1 M acetate buffer of pH 4.0 and a 1 M NaCl/0.1 M borate buffer of pH 8.4.

The last wash is carried out with 0.1 M borate buffer of pH 8.4, containing 0.5 M of NaCl and 0.005 M of EDTA.

(b) Isolation of the antigen-e

A column of 2 × 11 cm of Sepharose coupled to anti-e is used. The column is equilibrated with the buffer at ambient temperature. 25 ml of the solution containing the antigen-e obtained in Example 1 and diluted to ½ with the buffer are added and left for one hour at ½ C to favor maximum adsorption. The column is then brought to 4° C and washed with the borate buffer until the optical density of the fractions becomes zero. The antigen-e is eluted from the column by an 0.1 M phosphate buffer of pH 10.8. The fractions containing the antigen-e, determined by measuring the optical density at 280 nm, are immediately brought to a physiological pH by adding 2 N HCl.

All these fractions are combined and concentrated by ultrafiltration on an Amicon molecular weight 30,000 filter.

The experiments carried out show that the product obtained does not contain antigen Australia.

By way of precaution, the preparation of Ag-e can be subjected to an attenuation with formaldehyde, beta-propiolactone or ultraviolet rays in order to remove any possible residual infectiousness without destroying the antigenicity.

The absence of infectiousness and the efficiency of this preparation are evaluated by experiments on chimpanzees. These experiments in particular comprise investigating a viral replication by determining the antigen Australia and the anti-HBs antibodies, the study of the transaminases and a histological monitoring by liver biopsy.

The administration of this preparation makes it possible to cause anti-e antibodies to appear in volunteer donors, and the blood originating from these donors can act as the starting material for obtaining purified fractions containing anti-e antibody, as described below, in Example 3.

EXAMPLE 3:

Preparation of a gamma-globulin fraction containing anti-e antibodies

The starting material is a defibrinated plasma obtained by plasmapheresis and originating from selected donors of which the blood contains anti-e antibodies. Ethanol is added to the plasma up to a concentration of 19%, at pH 5.85 and at a temperature of −5° C, the volumes being so chosen as to give a final concentration of proteins of about 5%. The mixture is centrifuged and a precipitate is isolated, which contains all the gamma-globulins and a part of the alpha- and beta-globulins.

The precipitate is suspended in water at 0° C at the rate of 10 liters of water for each kilogram of precipitate. The pH is adjusted to 4.6 by adding a buffer mixture of pH 4 obtained by mixing one volume of 0.05 M $Na_2HPO_4$ and six volumes of 0.05 M acetic acid.

Thereafter, a buffer of pH 4.8 composed of one volume of 0.05 M $Na_2HPO_4$ and of 1.65 volumes of 0.05 M acetic acid is added in order to increase the ionic strength. It is necessary to add about 2.35 liters of buffer at pH 4.

Thereafter, the pH is adjusted to 5.1 by adding about 4.5 liters of a buffer obtained by mixing one volume of 0.05 M $Na_2HPO_4$ and 0.83 volume of 0.05 M acetic acid, while maintaining the temperature at −5° C.

The ionic strength is adjusted by adding 0.4 liter of a buffer of pH 5.1 consisting of one volume of 0.05 M $Na_2HPO_4$ and 1.25 volumes of acid.

The suspension is then diluted with 9.7 liters of water. This gives a total volume of solvent of 19.45 liters for each kilogram of precipitate.

Ethanol is added until an ethanol concentration of 12% is obtained.

The mixture is centrifuged and the supernatant liquor is collected. Sodium chloride is added until an ionic strength of between 0.03 and 0.04 is obtained. Thereafter, the pH is adjusted to 7.2 and ethanol is added until a concentration of 25% is reached, at a temperature of −7° C. A precipitate of gamma-globulins is obtained, which is collected by centrifuging. The final medicament is then prepared by the usual methods, that is to say by dissolving, clarification and lyophilization, followed by the preparation of a 16% strength aqueous solution. In order to obtain an isotonic solution which gives better solubility and better stability, 0.3 mol of glycine is added per liter. 0.1 g per liter of merthiolate is also added as a preservative.

The supplementary treatments, for the purpose of obtaining gamma-globulins which can be injected intravenously, can also be carried out in accordance with the usual processes.

EXAMPLE 4:

Preparation of a gamma-globulin fraction rich in anti-$e_1$ antibodies

On following the procedure of Example 3, but starting from plasmas selected because of their richness in anti-$e_1$ antibodies, a gamma-globulin fraction rich in anti-$e_1$ antibodies is obtained, and is stored in a lyophilized form.

EXAMPLE 5: Preparation of a gamma-globulin fraction rich in anti-$e_2$ antibodies On following the procedure of Example 3, but starting from plasmas selected because of their richness in anti-$e_2$ antibodies, a gamma-globulin fraction rich in anti-$e_2$ antibodies is obtained, and is stored in a lyophilized form.

We claim:

1. A medicament which contains, in a physiologically acceptable medium, a gamma-globulin preparation containing an effective amount of anti-e antibodies, the said preparation being obtained from serum or blood plasma or from placentary extracts and the said preparation being free from substantially all normal blood protein constituents other than gamma-globulins and from substantially all infectious contaminants.

2. A medicament according to claim 1 in which the gamma-globulin preparation has been subjected to a treatment to eliminate or reduce its anticomplementary power.

3. A medicament according to claim 2, which consists of blood, of plasma or of any other biological liquid to which the gamma-globulin preparation has been added.

4. A medicament according to claim 1 in which the said gamma-globulin preparation contains predominantly one of the anti-e antibodies.

5. A medicament according to claim 4, in which the said gamma-globulin preparation contains predominantly anti-$e_1$ or anti-$e_2$ antibodies.

6. A process for the treatment of hepatitis or acute or chronic infections caused by the virus of hepatitis B comprising administering intramuscularly or intravenously to an infected human or animal the medicament of claim 1.

7. A process for eliminating or reducing the infectiousness of a biological liquid which contains the virus of hepatitis B or antigen-e comprising contacting said liquid with a gamma-globulin preparation containing an effective amount of anti-e antibodies, the said preparation being obtained from serum or blood plasma or from placentary extracts and the said preparation being free from substantially all normal blood protein constituents other than gamma-globulins and from substantially all infectious contaminants.

8. A process according to claim 7, in which the said gamma-globulin preparation containing anti-e antibodies is added to the said liquid.

9. A process according to claim 7 in which the said liquid is passed over an immuno-adsorbent, the surface of which is lined with anti-e antibodies.

* * * * *